(12) United States Patent
Chaung et al.

(10) Patent No.: US 9,121,848 B2
(45) Date of Patent: Sep. 1, 2015

(54) CHINESE HERBAL AQUEOUS EXTRACT HAVING ANTI-ANXIETY ACTIVITIES AND METHOD OF IN VITRO EVALUATING THE SAME

(71) Applicant: NATIONAL PINGTUNG UNIVERSITY OF SCIENCE AND TECHNOLOGY, Pingtung (TW)

(72) Inventors: Hso-Chi Chaung, Pingtung County (TW); Tsung-Hui Yang, Pingtung County (TW); Holi Chen, Pingtung County (TW); Chih-Cheng Chen, Pingtung County (TW); Hsien-Hsueh Chiu, Pingtung County (TW)

(73) Assignee: NATIONAL PINGTUNG UNIVERSITY OF SCIENCE AND TECHNOLOGY, Pingtung (TW)

( * ) Notice: Subject to any disclaimer, the term of this patent is extended or adjusted under 35 U.S.C. 154(b) by 0 days.

(21) Appl. No.: 14/676,915

(22) Filed: Apr. 2, 2015

(65) Prior Publication Data

US 2015/0204854 A1 Jul. 23, 2015

Related U.S. Application Data

(62) Division of application No. 13/208,533, filed on Aug. 12, 2011.

(30) Foreign Application Priority Data

Feb. 25, 2011 (TW) .............................. 100106448 A

(51) Int. Cl.
| | |
|---|---|
| A61K 36/00 | (2006.01) |
| A61K 36/254 | (2006.01) |
| A61K 36/725 | (2006.01) |
| G01N 33/50 | (2006.01) |

(52) U.S. Cl.
CPC .......... *G01N 33/5058* (2013.01); *A61K 36/254* (2013.01); *A61K 36/725* (2013.01); *G01N 33/502* (2013.01); *G01N 2333/415* (2013.01); *G01N 2500/10* (2013.01)

(58) Field of Classification Search
None
See application file for complete search history.

(56) References Cited

U.S. PATENT DOCUMENTS

2002/0142287 A1 10/2002 Yamamoto et al.

FOREIGN PATENT DOCUMENTS

| CN | 1685941 A | 10/2005 |
|---|---|---|
| CN | 101822792 A | 9/2010 |
| KR | 2001000470 A | 1/2001 |
| WO | 2008009131 A1 | 1/2008 |

OTHER PUBLICATIONS

"The effect of acanthopanax senticosus in water-effect and function of acanthopanax senticosus and eating method thereof" Chengdu Tea Net, May 27, 2010.
"Tranquilizing mind, dispersing and rectifying the depressed liver-enery, the most important of recuperating from anxiety disorders" Net of China Daily Medicine, Dec. 6, 2010.
"Treating generalized anxiety disorder with acanthopanax senticosus harms injection for intravenous infusion" Hebei Mental Health, 2000, 13(1).
"Pharmacological study on effect of acanthopanax bark" Medical Education Net, Sep. 25, 2009.
"Brain Cannabinoids in Chocolate", Scientific Correspondence, Nature, vol. 382, Aug. 22, 1996, pp. 677-678.
Zhuang et al. "Cannabinoids produce neuroprotection by reducing intracellular calcium release from ryanodine-sensitive stores" Neuropharmacology 48 (2005) 1086-1096.
Chia-Jung Chang, "Effects of Docosahexaenoic Acid and Phosphatidylserine on Gene Expression of Neurexin II and Neuronal Apoptosis" Master Thesis, National Pingtung University of Science and Technology. Jun. 19, 2009.
Abricio A. Moreira and Maximilian Grieb, "Central side-effects of therapies based on CB1 cannabinoid receptor agonists and antagonists: focus on anxiety and depression" Best Practice & Research Clinical Endocrinology & Metabolism 23 (2009) 133-144.
Moreira et al, Reduced anxiety-like behaviour induced by genetic and pharmacological inhibition of the endocannabinoid-degrading enzyme fatty acid amide hydrolase (FAAH) is mediated by CB1 receptors. Neuropharmacology, (Jan. 2008) vol. 54, No. 1, pp. 141-150.

*Primary Examiner* — Qiuwen Mi
(74) *Attorney, Agent, or Firm* — McClure, Qualey & Rodack, LLP

(57) ABSTRACT

A Chinese herbal aqueous extract having anti-anxiety activities and a method of in vitro evaluating the same are disclosed. Neural cells and/or glial cells are cultured in a medium containing the Chinese herbal aqueous extract, and then subjected to an electric pulse treatment to form epileptic cells. The epileptic cells are applied on evaluation of at least one criterion of anti-anxiety activities of the Chinese herbal aqueous extract.

11 Claims, 11 Drawing Sheets

CHINESE HERBAL AQUEOUS EXTRACT HAVING ANTI-ANXIETY ACTIVITIES AND METHOD OF IN VITRO EVALUATING THE SAME

RELATED APPLICATIONS

This is a divisional application of U.S. application Ser. No. 13/208,533, filed Aug. 12, 2011, which is herein incorporated by reference, which was based on, and claims the benefit of, and priority to, Taiwan Application Serial No. 100106448, filed Feb. 25, 2011, the entire disclosures of which are hereby incorporated by reference in their entireties.

BACKGROUND

1. Field of Invention

The present invention relates to an active substance having anti-anxiety activities and a method of evaluating the same. More particularly, the present invention relates to a Chinese herbal aqueous extract and a method of in vitro evaluating anti-anxiety activities of the same.

2. Description of Related Art

Animal central nervous system (CNS) has many kinds of receptor systems for receiving and responding signals that generate from body under environmental changes. Some active natural components, which can keep spirit and mind health, perhaps function on many CNS receptors including cannabinoid receptor 1 (CB1) and other receptors. However, the nervous system suffers injury under oxidative pressure and hyper-excitatory electrical potential. Therefore, reduction of oxidative pressure and hyper-excitatory electrical potential is helpful to maintain the cell activity of the neural cells and the glial cells of the nervous system.

CB1 receptors are discovered in recent years and mainly distributed in portions of the CNS. Those portions that include hippocampus, amygdala, anterior cingulated cortex and prefrontal cortex are directly associated with emotional management and behaviors. Physiological ligands of CB1 receptors are arachidonic acid (AA) derivatives, and endogenous CB1 ligands mainly include N-arachidonoylethanolamine (anadamide) and 2-arachidonoyl glycerol (2-AG). The physiological functions of CB1 ligands can reduce pain and anxiety, increase reward and help for sleepiness. The animal experiments evidence that the anxiety is induced by blocking of CB1 receptor activation or in CB1 receptor knockout mice. Such anxiety cannot be effectively improved even through the administration of anti-anxiety drugs. These evidences indicate that the CB1 receptors have a significant impact on emotional management.

Researchers such as di Tomaso E. et al. had published a report titled as "Brain cannabinoids in chocolate" See di Tomaso E. et al. *Nature* 382(6593):677-678 (1996). This report evidenced that some active constituents of chocolate increased the concentration of endogenous CB1 ligands of the CNS, thereby producing a transient feeling of well-being. In addition, human milk also includes high amount of endogenous CB1 ligand, 2-AG. Other studies demonstrated that 2-AG is a very important bioactive factor for maintaining orexis and increasing survival rate of newborn animals.

However, the existing chemical drugs of anti-anxiety drugs or sleeping drugs have some disadvantages, such as temporary and permanent amnesia in long-term usage due to high effect concentration and most stimulation of the inhibitory potential of such drugs. As a result, scientists shifted to find naturally anti-anxiety active substances from plants. AA derivatives are not existed in plants, whereas more than three hundred kinds of plant fatty acid N-alkylamides (FAAs) have similar structures and biosynthesis routes with endogenous CB of animals. Among these compounds, many plants selected for reducing pain and inflammation contain active constituents that can bind to CB2 receptors. CB2 receptors are mainly distributed on immune cells, and the active constituents can affect animal immune cells through the CB2 receptors. Although there are many Chinese herbal medicines for helping tranquilization and anti-anxiety, the mechanism and related receptors of these active constituents are not clear. Moreover, there is no effective, quick and economic in vitro evaluation method for fast screening natural anti-anxiety active constituents from numerous raw materials of Chinese herbal medicines.

Therefore, it is necessary to provide an effective and precise in vitro evaluating method, thereby finding natural anti-anxiety active constituents from numerous raw materials of Chinese herbal medicines.

SUMMARY

A method of in vitro evaluating Chinese herbal aqueous extract with anti-anxiety activity is provided. The method comprises the steps of culturing a neural cell and/or a glial cell in a testing medium that includes the Chinese herbal aqueous extract. And then, an electric pulse treatment is applied on the neural cell and/or the glial cell, so as to form an epileptic cell. Later, at least one anti-anxiety parameter of the epileptic cell is detected and compared with respect to the reference value, so as to evaluate the anti-anxiety activity of the Chinese herbal aqueous extract. In addition, the animal experimentation has also verified that the Chinese herbal aqueous extract evaluated in vitro has the anti-anxiety activity in vivo.

Moreover, a Chinese herbal aqueous extract with anti-anxiety activity is provided. The Chinese herbal aqueous extract, which is evaluated by using the aforementioned method, can enhance a membrane expression of a Cannabinoid receptor type-1 (CB1).

Furthermore, a food composition is provided. The food composition comprises the Chinese herbal aqueous extract and at least one food additive.

Accordingly, the invention provides a method of in vitro evaluating Chinese herbal aqueous extract with anti-anxiety activity. In an embodiment, the method comprises the steps of extracting a raw material of a Chinese herbal medicine sample with hot water, so as to obtain a Chinese herbal aqueous extract, wherein the Chinese herbal aqueous extract is a test sample. Next, a neural cell and/or a glial cell are cultured in a testing medium that includes the test sample or not. And then, an electric pulse treatment is applied on the neural cell and/or the glial cell to be suffered with a hyper-excitatory electrical potential injury, thereby forming an epileptic cell. Afterwards, at least one anti-anxiety parameter of the epileptic cell is detected, in which the anti-anxiety parameter comprises a cell viability, a percentage of reactive oxygen species (ROS)-generated cells and a percentage of apoptotic cells, and at least one test value is defined to the at least one anti-anxiety parameter obtained from the epileptic cell cultivated with the test sample, and at least one reference value is defined to the at least one anti-anxiety parameter obtained from the epileptic cell cultivated without the test sample. After that, the test value is compared with the reference value, so as to determine that the test sample has the anti-anxiety activity based on when the cell viability is more than the reference value, as well as the percentage of the ROS-generated cells and the percentage of apoptotic cells are less than the reference.

According to an embodiment of the invention, the aforementioned neural cell, the glial cell or the combination thereof includes a neuroblastoma cell line, a glioblastoma cell line or the combination thereof.

According to an embodiment of the invention, the aforementioned electric pulse treatment is applied on the neural cell and/or the glial cell by using 5 mV of pulse voltage and 100 ms of inter-pulse interval for 50 times continuously.

According to an embodiment of the invention, the aforementioned Chinese herbal aqueous extract with anti-anxiety activity is extracted from Poris Cum (PC), Semen Biotae Orientalis (SBO), Acanthopanacis Cortex (AC) or Semen Zizyphi Spinosae (SZS).

According to an embodiment of the invention, an expression amount of a Cannabinoid receptor type-1 (CB1) is enhanced in vivo by the aforementioned Chinese herbal aqueous extract with anti-anxiety activity.

Moreover, the invention further provides a Chinese herbal aqueous extract with anti-anxiety activity, which includes the Chinese herbal aqueous extract obtained by using the aforementioned method.

In addition, the invention further provides a food composition that includes the aforementioned Chinese herbal aqueous extract and at least one food additive.

With application of the Chinese herbal aqueous extract having anti-anxiety activities and the method of in vitro evaluating the same, which use the epileptic cells as an evaluation platform for screening the Chinese herbal aqueous extract having anti-anxiety activities. Moreover, the evaluated Chinese herbal aqueous extract indeed has anti-anxiety activities and enhancement of CB1 membrane expression evidenced by the animal experimentation, thereby being applied in food or other compositions.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
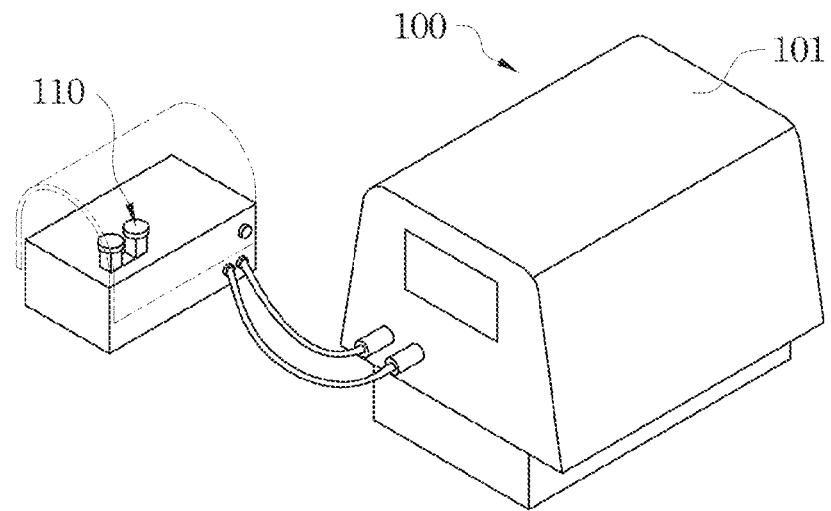
FIGS. 1A and 1B show schematic diagrams of the electroporator (FIG. 1A) and its electroporator cuvette (FIG. 1B) according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the invention relates to a Chinese herbal aqueous extract having anti-anxiety activities and a method of in vitro evaluating the same, which use the epileptic cells as an evaluation platform for screening the Chinese herbal aqueous extract having anti-anxiety activities in quick, economical and precise ways.

In Vitro Evaluating Chinese Herbal Aqueous Extract Having Anti-Anxiety Activities The "Chinese Herbal Aqueous Extract" as discussed hereinafter is referred to the one obtained by using hot eater extraction of a raw material of a Chinese herbal medicine sample. In detail, in an embodiment, the raw material of the Chinese herbal medicine sample is mixed with sterile water, heated to boiling and kept heating for about 105 minutes. It is noted that, if the water temperature is below the boiling point or the heating duration is insufficient, the bioactive component having anti-anxiety activities could not be extracted from the raw material of the Chinese herbal medicine sample. However, if the water temperature is above the boiling point or the heating duration is more than the aforementioned heating time, the bioactive component having anti-anxiety activities in the raw material of the Chinese herbal medicine sample could be destroyed.

After the heating step, the solid component (or residual) of the raw material of the Chinese herbal medicine sample can be removed by using conventional methods such as filtration, solid-liquid separation or other methods, followed by removing water in the raw material of the Chinese herbal medicine sample through rotary evaporation and/or lyophilization, thereby obtaining powder of the Chinese herbal aqueous extract. The powder of the Chinese herbal aqueous extract can be prepared to a concentrated aqueous solution (e.g. 10 g/L) by rehydrating with water or aqueous solution. In the subsequent evaluation steps, the Chinese herbal aqueous extract is a test sample for adding into a testing medium. The testing medium has an amount of 0.01 g/L to 1 g/L, 0.05 g/L to 0.51 g/L, or about 0.1 g/L.

Next, in an embodiment, a neural cell and/or a glial cell can be cultured in testing medium that includes the test sample or not and incubated in a condition at 37° C. in 5% $CO_2$. In an example, the aforementioned neural cell and/or a glial cell is referred to the neural cell, the glial cell or the combination thereof, which include any available neuroblastoma cell line, glioblastoma cell line or the combination thereof. For example, the neural cell includes but is not limited to human neuroblastoma cell line IMR-32 (deposited at the American Type Culture Collection (ATCC) under accession No.: ATCC CCL-127), the glial cell includes but is not limited to human glioblastoma cell line U-87 MG (deposited at ATCC under accession No.: ATCC HTB-14), and the two cells are purchased from the Food Industry Research and Development Institute (FIRDI), Bioresource Collection and Research Center (BCRC), Hsinchu, Taiwan). Also, the neural cell and the glial cell obtained from other sources can be used in the present invention. In another example, the neural cell and the glial cell cultured in the medium with the test sample belong to an experimentation group, and the neural cell and the glial cell cultured in the medium without the test sample belong to a control group.

For the purpose of evaluating the protection effect of the Chinese herbal aqueous extract to the neural cell and/or the glial cell, the present invention utilizes an electric pulse technology to establish an epileptic cell as in vitro evaluation platform. The epileptic cell is generated from human neural cell and/or human glial cell that are treated with a hyper-excitatory electrical potential injury. Some physiological activities such as CB1 membrane expression, cell viability, physiological activity and anti-anxiety activity of the epileptic cell are then detected in vitro, so as to evaluate the in vitro protection effect of the Chinese herbal aqueous extract to the neural cell and/or the glial cell under the condition of oxidative stress or hyper-excitatory electrical potential injury.

In an embodiment, when the neural cell and/or the glial cell are cultured after about 12 to about 36 hours, or after about 24 hours, the neural cell and/or the glial cell are subjected to an electric pulse treatment, allowing the neural cell and/or the glial cell to be suffered with a hyper-excitatory electrical potential injury, thereby forming an epileptic cell. In an embodiment, during the electric pulse treatment, a commercially available electroporator can apply 5 mV of pulse voltage and 100 ms of inter-pulse interval on the neural cell and/or the glial cell for 50 times continuously. The neural cell and/or the glial cell are suffered with the hyper-excitatory electrical potential injury that decreases 50% cell viability of those cells. If the neural cell and/or the glial cell were treated with other conditions rather than using the aforementioned ones during the electric pulse treatment, the neural cell and the glial cell could not be qualified as the screening platform due to the following reasons, for example, the epileptic cells that cannot be simultaneously formed with 30% to 50% cell injury from the neural cell and the glial cell, the ROS-positive cells increased in at least 2 times to 10 times, insufficient cell injury, or excessively injured cells that cannot be self-repaired. Those unqualified cells cannot provide convincible results in subsequent evaluation process.

And then, at least one anti-anxiety parameter of the epileptic cell is detected. In an example, the anti-anxiety parameter comprises cell viability, percentage of ROS-generated cell, percentage of apoptotic cells and other distinguishable characteristics. Among those, at least one test value is defined to the at least one anti-anxiety parameter obtained from the epileptic cell cultured with the test sample (i.e. the experimental group), and at least one reference value is defined to the at least one anti-anxiety parameter obtained from the epileptic cell cultivated without the test sample (i.e. the control group).

Later, the test value is compared with the reference value, so as to determine that the test sample has the anti-anxiety activity. In an example, the test sample is determined to have the anti-anxiety activity based on when the experimental group has more cell viability, less percentage of the ROS-generated cells and less percentage of apoptotic cells than the reference value of the control group. A nervous system of an organism is injured when the organism is subjected to the oxidative stress or the hyper-excitatory electrical potential. However, if the Chinese herbal aqueous extract can reduce the oxidative stress and the excitatory electrical potential of the epileptic cell, the Chinese herbal aqueous extract is determined to have the anti-anxiety activity so that it is beneficial to maintain the cell viability of the neural cells and the glial cells in the nervous system.

Chinese Herbal Aqueous Extract with Anti-Anxiety Activity

In an embodiment, the Chinese herbal aqueous extract with anti-anxiety activity, which has been evaluated by the aforementioned method, can be extracted from *Poris Cum* (PC), *Semen Biotae Orientalis* (SBO), *Acanthopanacis Cortex* (AC) or *Semen Zizyphi Spinosae* (SZS). In another embodiment, CB1 membrane expression can be enhanced in vivo by the Chinese herbal aqueous extract with anti-anxiety activity. In other embodiments, a food composition includes the evaluated Chinese herbal aqueous extract alone or mixed with at least one food additive.

Thereinafter, various applications of the Chinese herbal aqueous extract having anti-anxiety activities and a method of in vitro evaluating the same will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

EXAMPLE 1

Establishment of In Vitro Cell Platform

1. Cell Culture of Human Neuroblastoma Cell Line IMR-32 and Human Glioblastoma U-87 MG Human neuroblastoma cell line IMR-32 (deposited at ATCC under accession No.: ATCC CCL-127) and human glioblastoma U-87 MG (deposited at ATCC under accession No.: ATCC HTB-14) were purchased from the Food Industry Research and Development Institute (FIRDI), Bioresource Collection and Research Center (BCRC), Hsinchu, Taiwan). The cell lines IMR-32 and U-87 MG were cultured in the minimum essential medium (MEM; Gibco® BRL, Grand Island, N.Y.) that contained 2 mM L-glutamine, 1 mM non-essential amino acids, 10% fetal bovine serum (FBS), 0.1 mg/mL streptomycin and 0.5 mg/mL ampicillin. Those cells were incubated for 48 hours in an incubator (NUAIR NU4500, USA) with 5% $CO_2$ humidified atmosphere at 37° C., and changed with the fresh medium every two or three days. When those cells reached about 90% confluence, the cells were gently washed in phosphate buffer saline (PBS) and subjected to trypsinization (0.25% 1 mL trypsin-EDTA/plate) to single cells, so as to separate several cell plates or to subculture according to different experimental purposes.

2. Preparation of Chinese Herbal Aqueous Extract 600 g *Poris Cum* (PC), 112 g *Semen Biotae Orientalis* (SBO), 112 g *Acanthopanacis Cortex* (AC) or 112 g *Semen*

*Zizyphi Spinosae* (SZS) was separately heated with 2.25 L sterile water to keep it boiling for 105 minutes. After cooling down and removing solid residues, the primary aqueous extract such as 330 mL primary aqueous extract of PC, 420 mL primary aqueous extract of SBO, 380 mL primary aqueous extract of AC or 460 mL primary aqueous extract of SZS was obtained, respectively.

The resulted primary aqueous extracts were concentrated by using a rotary evaporator (BUCHI Rotavapor R-200, Switzerland), respectively, and then the secondary aqueous extract such as 134 mL secondary aqueous extract of PC, 53 mL secondary aqueous extract of SBO, 82 mL secondary aqueous extract of AC or 72 mL secondary aqueous extract of SZS was obtained, respectively. Later, the resulted secondary aqueous extracts were lyophilized by using a freeze drying system (Labconco Freezone dry system, USA), and then the Chinese herbal aqueous extract such as 14.17 g PC aqueous extract, 9.74 g SBO aqueous extract, 15.93 g AC aqueous extract or 12.75 g SZS aqueous extract was obtained, respectively.

100 mg of PC, SBO, AC or SZS aqueous extract was prepared to 10 mg/mL PC, SBO, AC or SZS aqueous extract solution, respectively.

3. Epileptic Cell Platform

After the cell line IMR-32 or U-87 MG is subjected to trypsinization (trypsin-EDTA/plate), the single cell solution was adjusted to cell density of $1 \times 10^6$ cells/mL, seeded into 96-well microplate with 100 μL cell solution per well (i.e. $1 \times 10^5$ cells/100 μL/well), and incubated for 24 hours in the incubator (NUAIR NU4500, USA) with 5% $CO_2$ humidified atmosphere at 37° C., and added with 1 μL PC, SBO, AC or SZS aqueous extract solution (i.e. 10 μg Chinese herbal aqueous extract/well), respectively. After being incubated for 24 hours in the incubator (NUAIR NU4500, USA) with 5% $CO_2$ humidified atmosphere at 37° C., the cells in each well were subjected to trypsinization (0.25% 20 μL trypsin-EDTA/well), and the trypsinized cells of each well were loaded into each electroporator cuvette (shown in FIG. 1B) of an electroporator (shown in FIG. 1A; BTX ECM830, USA) for being subjected to the electric pulse treatment.

Figure 1B:
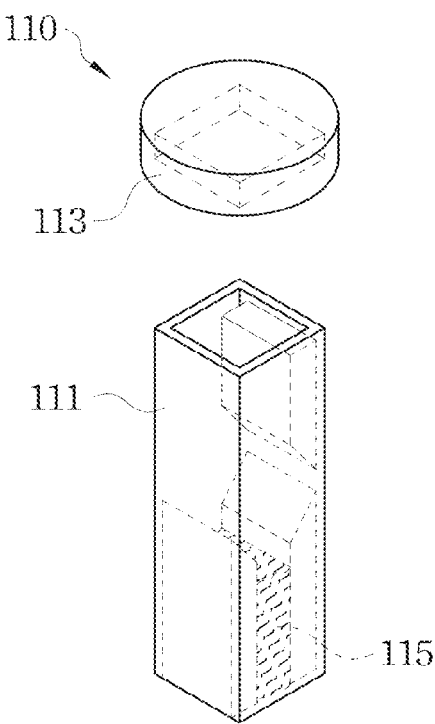

Reference is made to FIGS. 1A and 1B, which show schematic diagrams of the electroporator (FIG. 1A) and its electroporator cuvette (FIG. 1B) according to an embodiment of the present invention. The electroporator cuvette 110 has a cuvette body 111 and a cap 113. The cuvette body 111 receives the being-treated cell solution 115 therein. The cuvette body 111 further has an electrode plate (unshown). In this EXAMPLE, a main body 101 of the electroporator (FIG. 1A) applied 5 mV of pulse voltage and 100 ms of inter-pulse interval on the cells (for example, the cell solution 115) in the electroporator cuvette 110 (FIGS. 1A and 1B) for 50 times continuously through connection lines and related equipments, thereby forming epileptic cells. After the electric pulse treatment was completed, the cell solution was seeded into 96-well plates, incubated for about 60 minutes and washed with PBS. Subsequently, cell viability, percentage of ROS-generated cells, percentage of apoptotic cells and other distinguishable characteristics were analyzed by using MTT test or other methods.

EXAMPLE 2

In Vitro Evaluating Chinese Herbal Aqueous Extract

This EXAMPLE was directed to evaluate the anti-anxiety activities of the Chinese herbal aqueous extracts of EXAMPLE 1 in vitro by using the epileptic cell platform established by EXAMPLE 1.

1. Evaluation of Cell Viability

In this EXAMPLE, cell viability of EXAMPLE 1 was detected by using MTT test. At first, methylthiazoletetrazolium (MTT; Sigma, St. Louis, Mo., USA) solution was prepared by adding 5 mg MTT into 1 mL PBS. Next, each well (i.e. $1 \times 10^5$ cells/well) of 96-well microplate was added with 10 μL MTT solution, incubated for 24 hours in the incubator (NUAIR NU4500, USA) in the dark with 5% $CO_2$ humidified atmosphere at 37° C., and then centrifuged for 10 minutes in a rotation speed of 1,000×g at 4° C. The supernatant was discarded and 100 μL dimethyl sulfoxide (DMSO; Merck, Darmstadt, Germany) solution is added. The microplate was vibrated gently for 10 minutes. Absorbance at 550 nm ($OD_{550nm}$) of each well was detected by ELISA reader (Thermo, USA) for evaluating cell viability. The result was shown in FIGS. 2A and 2B.

Figure 2A:
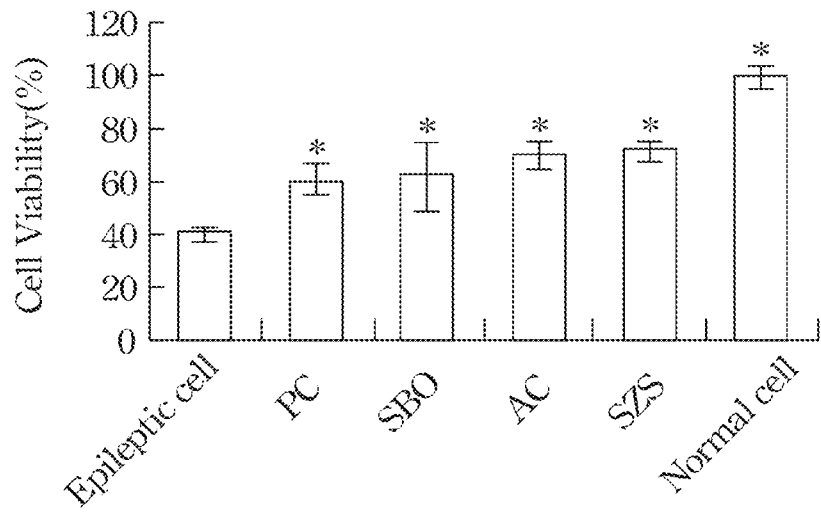
FIGS. 2A and 2B show histograms of the cell viability of the cell line IMR-32 (FIG. 2A) or U-87 MG (FIG. 2B) through the electric pulse treatment according to an embodiment of the present invention.
Figure 2B:
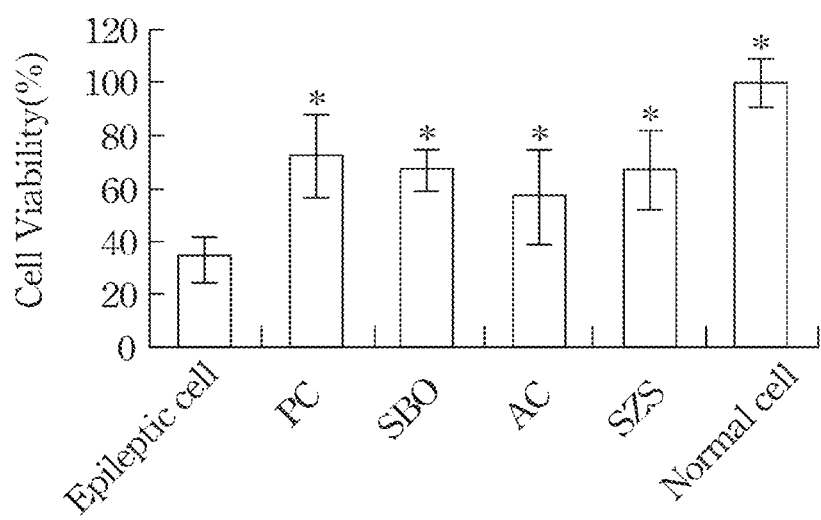

Reference is made to FIGS. 2A and 2B, which show histograms of the cell viability of the cell line IMR-32 (FIG. 2A) or U-87 MG (FIG. 2B) through the electric pulse treatment according to an embodiment of the present invention, in which the symbol "*" is referred to the statically significant difference of the cell viability values in the experimental group as compared with the control group (i.e. "Epileptic cell") ($P<0.05$).

Based on the results of FIGS. 2A and 2B, as compared with the normal cell (i.e. "Normal cell") that was untreated with the electric pulse treatment, the control group (i.e. "Epileptic cell") including the cell line IMR-32 (FIG. 2A) or U-87 MG (FIG. 2B) had significantly less cell viability. However, as compared with the control group (i.e. "Epileptic cell"), the epileptic cell line IMR-32 (FIG. 2A) or U-87 MG (FIG. 2B) treated with the PC, SBO, AC or SZS aqueous extract solution had significantly increased cell viability.

2. Evaluation of Percentage of ROS-Generated Cells

In this EXAMPLE, 10 mM/μL 2,7-dichlorofluorescein diacetate (H2DCF-DA; Invitrogen, USA) solution was prepared by adding H2DCF-DA into DMSO anhydrous. Next, the cell line IMR-32 or U-87 MG of EXAMPLE 1 was washed with PBS, added into PBS (including 10 μM H2DCF-DA) and incubated for 30 minutes in the incubator at 37° C. After being washed with PBS, the cells were recovered in phenol red-free MEM for 5 minutes in the incubator at 37° C. The cells were collected, and then the DCF (the fluorescent product of H2DCF-DA) fluorescence intensity at the emission wavelength of 526 nm (FL1) of each group was measured by using a FACScan flow cytometry (Beckman Coulter Epics XL-MCL, USA) at the excitation wavelength of 488 nm, so as to analyze the percentage of ROS-generated cells (%). The flow cytometric result was shown in FIG. 3.

Figure 3:
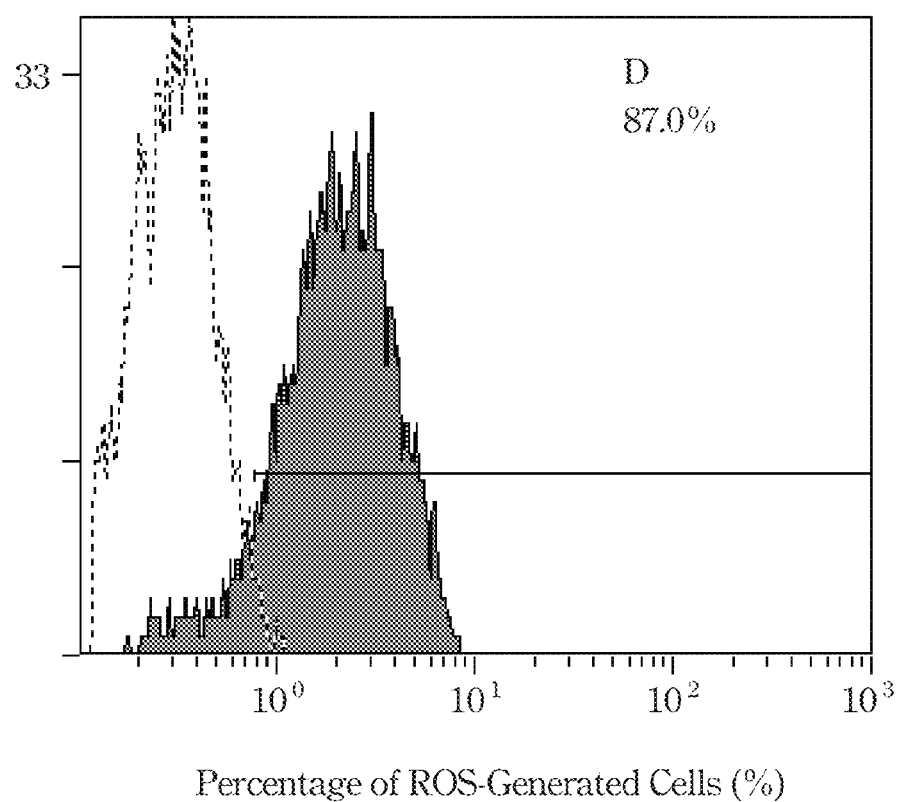
FIG. 3 shows a flow cytometric diagram with respect to the percentage of ROS-generated cells of the cell line IMR-32 or U-87 MG through the electric pulse treatment according to an embodiment of the present invention.

Reference is made to FIG. 3, which shows a flow cytometric diagram with respect to the percentage of ROS-generated cells of the cell line IMR-32 or U-87 MG through the electric pulse treatment according to an embodiment of the present invention, in which the open peak is referred to ROS-negative cells (i.e. the cells without generating ROS), the shaded peak is referred to ROS-positive cells (i.e. the cells with generating ROS), and the percentage presented in the region D is referred to the percentage of ROS-generated cells.

Figure 4A:
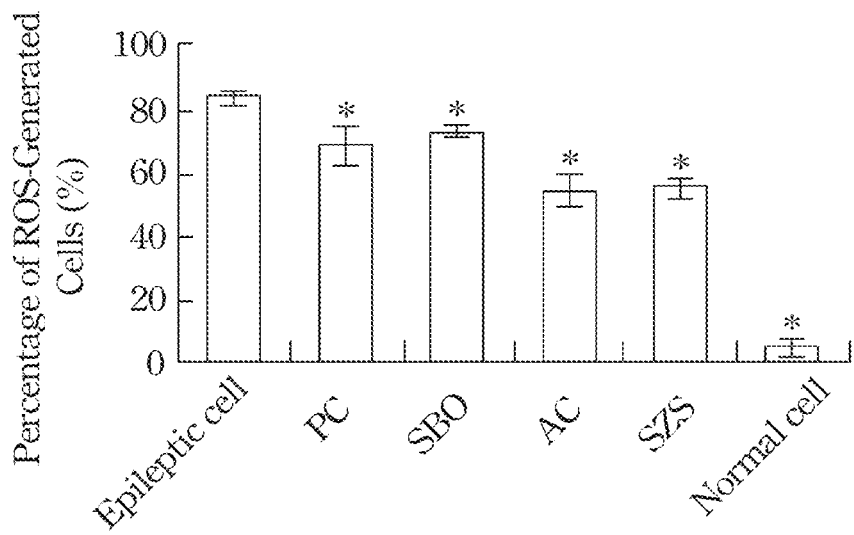
FIGS. 4A and 4B depict histograms with respect to the percentage of ROS-generated cells of the cell line IMR-32 (FIG. 4A) or U-87 MG (FIG. 4B) through the electric pulse treatment according to an embodiment of the present invention.
Figure 4B:
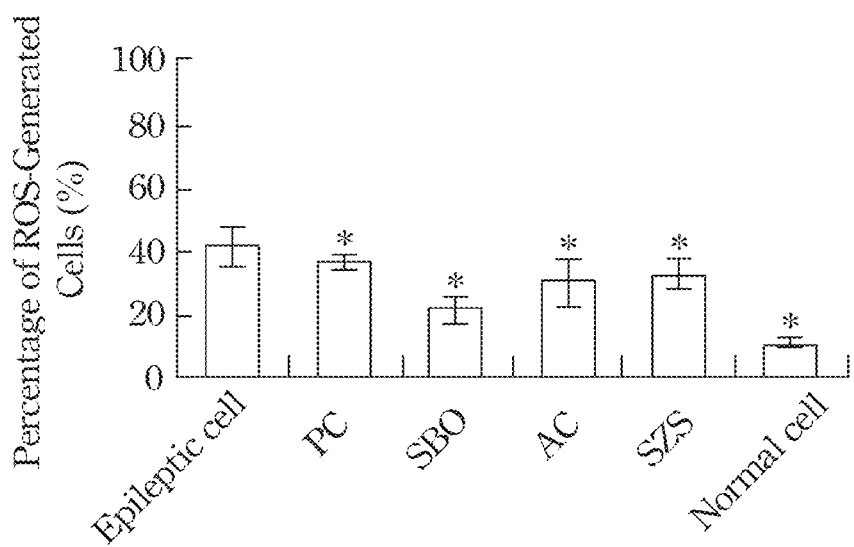

Reference is also made to FIGS. 4A and 4B, which depict histograms with respect to the percentage of ROS-generated cells of the cell line IMR-32 (FIG. 4A) or U-87 MG (FIG. 4B) through the electric pulse treatment according to an embodiment of the present invention, in which the symbol "*" is referred to the statically significant difference of the percentage of ROS-generated cells in the experimental group as compared with the control group (i.e. "Epileptic cell") ($P<0.05$).

Based on the results of FIGS. 4A and 4B, as compared with the normal cell (i.e. "Normal cell") that was untreated with the electric pulse treatment, the control group (i.e. "Epileptic cell") including the cell line IMR-32 (FIG. 4A) or U-87 MG (FIG. 4B) had significantly increased percentage of ROS-generated cells. However, as compared with the control group (i.e. "Epileptic cell"), the epileptic cell line IMR-32 (FIG. 4A) or U-87 MG (FIG. 4B) treated with the PC, SBO, AC or SZS aqueous extract solution had significantly reduced percentage of ROS-generated cells from the epileptic cells.

3. Evaluation of Percentage of Apoptotic Cells

In this EXAMPLE, the cell line IMR-32 or U-87 MG of EXAMPLE 1 was washed with PBS, collected into 1.5 mL eppendorf vials, respectively. Each vial is added with 100 μL annexin V-binding buffer of Vybrant® Apoptosis Assay Kit (Invitrogen, USA), 5 μL annexin V and 1 μL 0.15 mM propidium Iodide (PI) dye, and mixed well, and reacted at room temperature. Later, each vial is added with 400 μL annexin V-binding buffer and put on ice. Afterward, the fluorescence intensity at the wavelength of 488 nm and 595 nm was measured by using a FACScan flow cytometry (Beckman Coulter Epics XL-MCL, USA), in which the cells bound with annexin V (annexin V$^+$) were referred to apoptotic cells, and the cells stained with PI dye were referred to necrotic cells, so as to evaluate the percentage of apoptotic cells. The result of the percentage of apoptotic cells was shown in FIG. 5.

Figure 5:
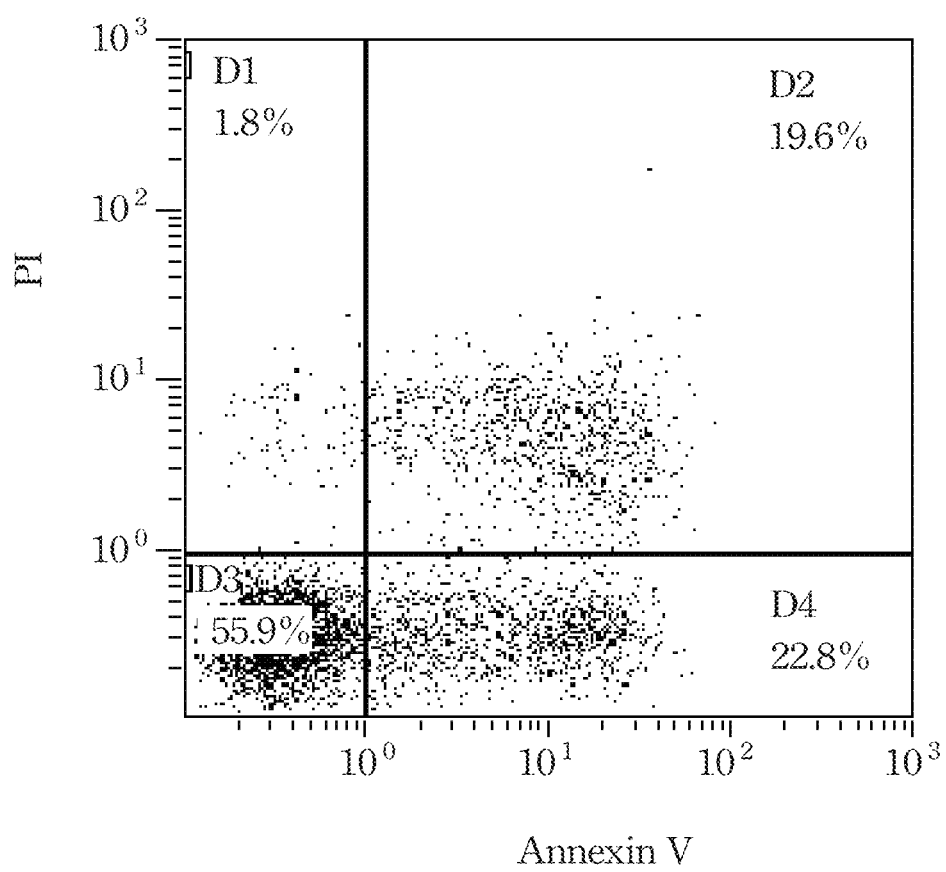
FIG. 5 depicts a two-dimensional dot pot with respect to the percentage of apoptotic cells of the cell line IMR-32 or U-87 MG through the electric pulse treatment according to an embodiment of the present invention.

Reference is also made to FIG. 5, which depicts a two-dimensional dot pot with respect to the percentage of apoptotic cells of the cell line IMR-32 or U-87 MG through the electric pulse treatment according to an embodiment of the present invention, in which the block D1 included PI$^+$ annexin V$^-$ cells (i.e. the necrotic cells), the block D3 included PI$^-$ annexin V$^-$ cells (i.e. the viable cells), the blocks D2 and D4 included annexin V$^+$ cells (i.e. the apoptotic cells).

Figure 6A:
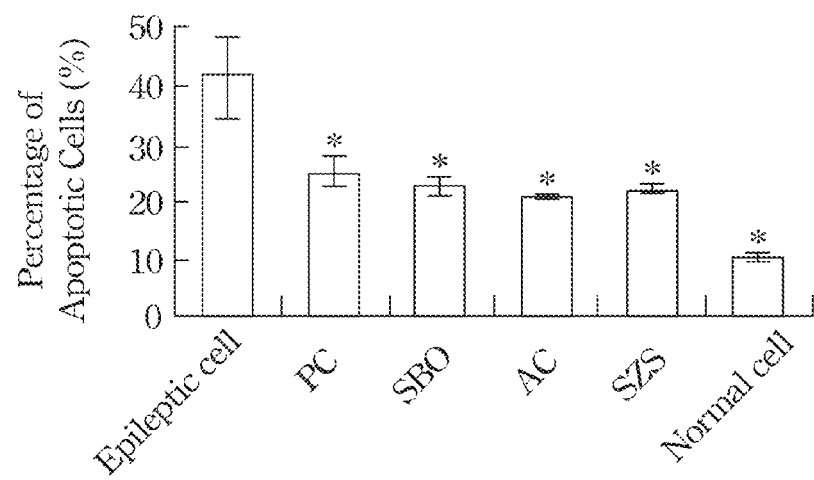
FIGS. 6A and 6B depict histograms of the percentage of apoptotic cells of the cell line IMR-32 (FIG. 6A) or U-87 MG (FIG. 6B) through the electric pulse treatment according to an embodiment of the present invention.
Figure 6B:
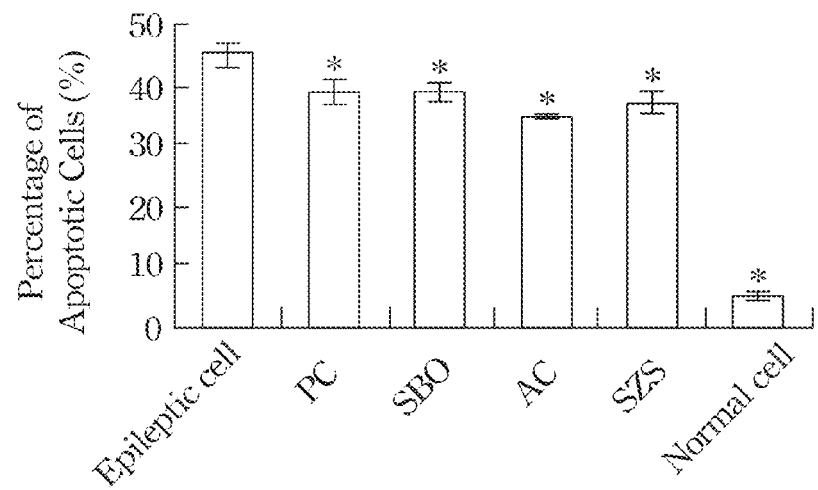

Moreover, reference is made to FIGS. 6A and 6B, which depict histograms of the percentage of apoptotic cells of the cell line IMR-32 (FIG. 6A) or U-87 MG (FIG. 6B) through the electric pulse treatment according to an embodiment of the present invention, in which the symbol "*" is referred to the statically significant difference of the percentage of apoptotic cells in the experimental group as compared with the control group (i.e. "Epileptic cell") ($P<0.05$).

Based on the results of FIGS. 6A and 6B, as compared with the normal cell (i.e. "Normal cell") that was untreated with the electric pulse treatment, the control group (i.e. "Epileptic cell") including the cell line IMR-32 (FIG. 6A) or U-87 MG (FIG. 6B) had significantly increased percentage of apoptotic cells. However, as compared with the control group (i.e. "Epileptic cell"), the epileptic cell line IMR-32 (FIG. 6A) or U-87 MG (FIG. 6B) treated with the PC, SBO, AC or SZS aqueous extract solution had significantly reduced percentage of apoptotic cells from the epileptic cells.

EXAMPLE 3

In Vivo Evaluating Anti-Anxiety Activities of Chinese Herbal Aqueous Extract by Using Experimental Animal Model This EXAMPLE was directed to evaluate the anti-anxiety activities of the Chinese herbal aqueous extracts of EXAMPLE 1 in vivo by using an animal model.

1. Establishment of Experimental Animals 1.1 Care of Experimental Animals

In this EXAMPLE, fifty six-week-old specific pathogen-free (SPF) imprinting-control-region (ICR) mice (purchased from BioLASCO Taiwan Co., Ltd., Yi-Lan, Taiwan) were randomly allocated into four experimental groups (i.e. PO group, SBO group, AC group and SZS group) and one control (PBS) group, each group of which had ten mice.

All ICR mice were bred in a SPF environment with positive air pressure. Ambient temperature was controlled at 24° C., relative humidity at 65±5. In addition, the animals were maintained on a reverse 12 h light-dark cycle. Mice were provided with standard laboratory chow and water ad libitum. All experimental procedures were performed according to the NIH Guide for the Care and Use of Laboratory Animals.

1.2 Feeding with Chinese Herbal Aqueous Extract

Figure 7A:
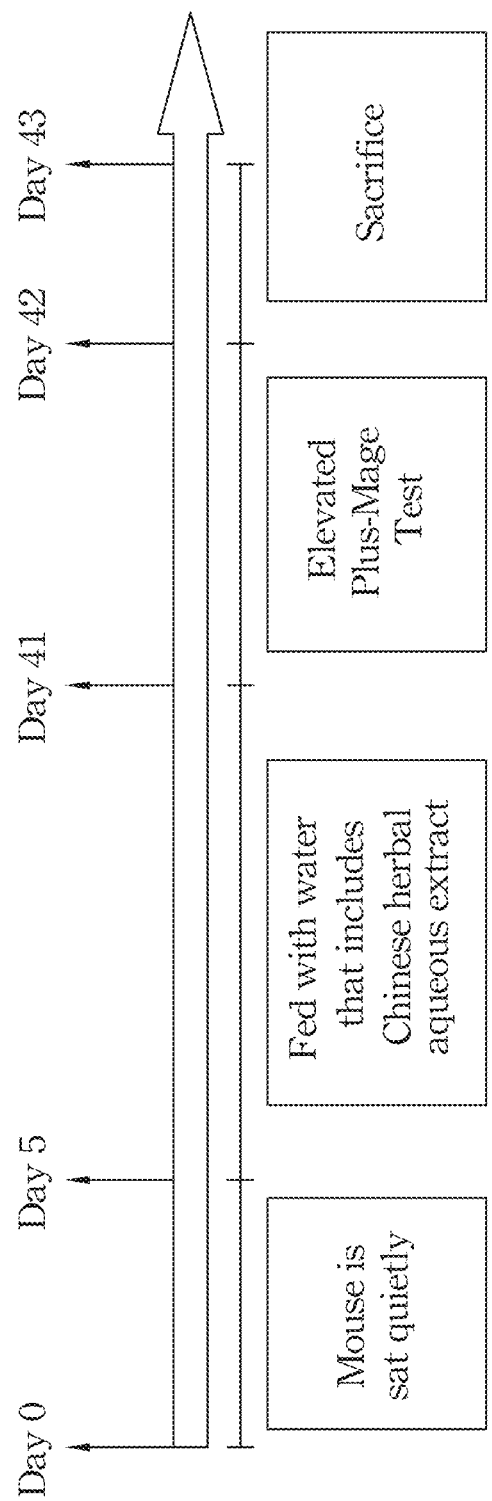
FIG. 7A depicts a flow chart of the animal test process according to an embodiment of the present invention.

Chinese herbal aqueous extracts of EXAMPLE 1 were prepared to solutions by adding the Chinese herbal aqueous extract into sterile water. The ICR mice of the four experimental groups were given 100 mg of Chinese herbal aqueous extract of EXAMPLE 1 per kg body weight once per day by oral administration (for example, orogastric intubation) for continuing 35 days. The ICR mice of the control group were orally administrated with distilled water or PBS once per day. The whole flow chart of the animal test process was shown in FIG. 7A.

Figure 7B:
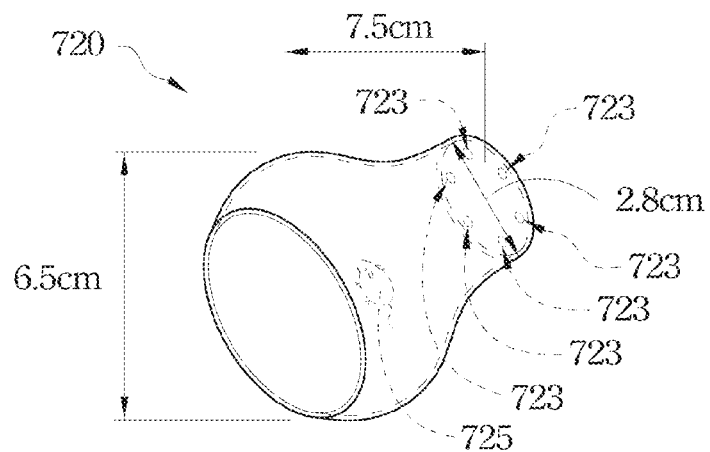
FIG. 7B depicts a stereo diagram of the closed environment according to an embodiment of the present invention.

2. Evaluation of Anti-Anxiety Behaviors of Experimental Animals 2.1 Establishment of Closed Environments This EXAMPLE is designed to direct the ICR mouse into a closed environment, inducing them to generate anxiety state. Reference is made to FIG. 7B, which depicts a stereo diagram of the closed environment according to an embodiment of the present invention. The ICR mouse 725 was firstly entered into the closed environment 720 of FIG. 7B before carrying the subsequent plus-maze test. In this EXAMPLE, the volume of the closed environment 720 was about 110 cm$^3$, and several air outlets 723 (for example, six air outlets with diameter of about 1 mm) are installed on the plastic plug. The closed duration is one hour, so as to make the ICR mouse 725 to generate anxiety state.

2.2 Elevated Plus-Maze

After the ICR mouse generated anxiety state, the ICR mouse was moved to an elevated plus-maze for one hour, allowing the mouse to adapt this environment.

Figure 7C:
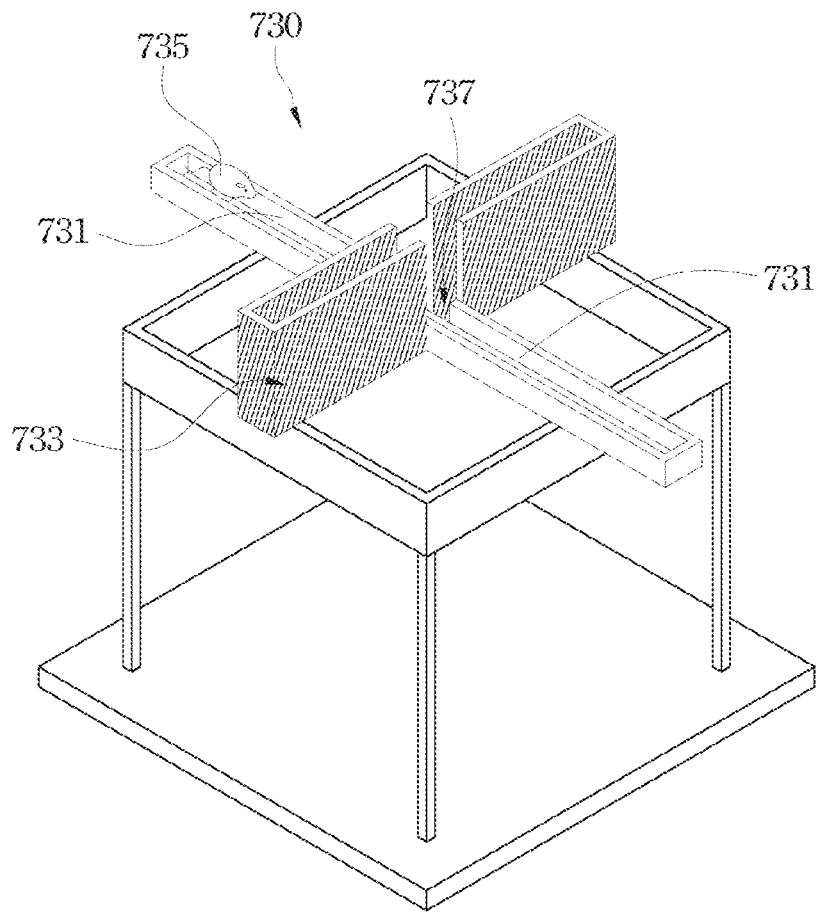
FIG. 7C depicts a stereo diagram of the elevated plus-maze according to an embodiment of the present invention.

Reference is made to FIG. 7C, which depicts a stereo diagram of the elevated plus-maze according to an embodiment of the present invention. The elevated plus-maze 730 is widely applied in an animal behavior test for measuring anxiety of an experimental animal. Anxiety associated behavior of the ICR mouse 735 was determined by counting the times that the ICR mouse 735 entered or stayed in open arms 731 or closed arms 733 as well as the duration time that the ICR mouse 735 spends in each arm. The open arms 731 were heightened and openly, and the closed arms 733 were sheltered by black plates. The elevated plus-maze 730 was elevated about 50 cm from the floor and lit it by dim light, the ICR mouse 735 must have been not subjected to such a test.

The ICR mouse having anxiety state was placed in the center 737 of the elevated plus-maze 730 and the test was started. The ICR mouse behavior was recorded by an animal behavior tracking system (for example, EthoVision XT system) and monitored by a camera (for example, DSP CCD CAMERA). The test was spent 5 minutes for counting the times and the duration time that the ICR mouse 735 freely entered or stayed in open arms 731 or closed arms 733. The anxiety of the ICR mouse 735 was compared by measuring the proportion of the duration time that the ICR mouse 735 spent in open arms 731 (i.e. time in open arms/total duration time), The times of the ICR mouse 735 entered into open arms 733 were counted for evaluating the ICR mouse 735 activity. However, it should be supplemented that, the anxiety of the comparison must be based on the condition that the ICR mouse 735 had little difference of activity.

Figure 8A:
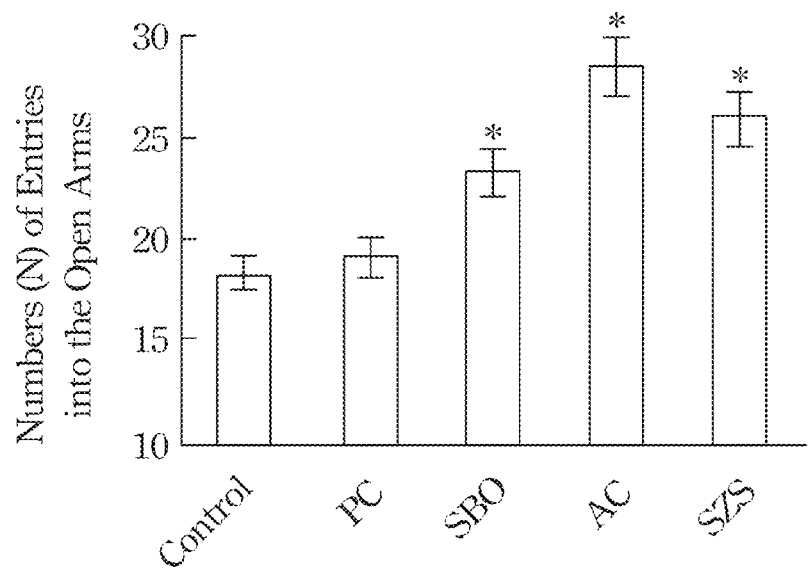
FIGS. 8A and 8B depict histograms of times of the ICR mouse entered in open arms (FIG. 8A) or closed arms (FIG. 8B) according to an embodiment of the present invention.
Figure 8B:
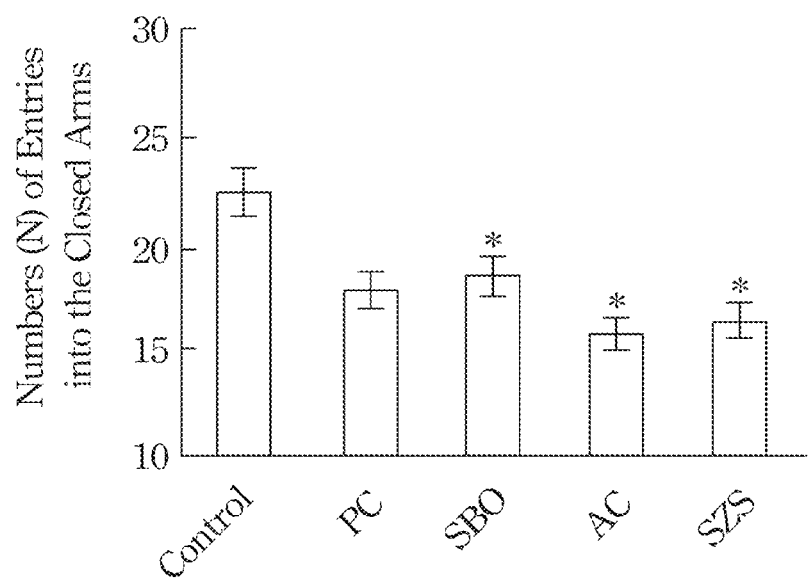

Reference is made to FIGS. 8A and 8B, which depict histograms of times of the ICR mouse entered in open arms (FIG. 8A) or closed arms (FIG. 8B) according to an embodiment of the present invention, in which the symbol "*" is referred to the statically significant difference of the averaged times of the experimental group as compared with the control group (i.e. "Epileptic cell") ($P<0.05$).

Based on the results of FIGS. 8A and 8B, as compared with the mice of the control group that were fed without the Chinese herbal aqueous extracts, the mice of the experimental groups (i.e. PC, SBO, AC and SZS groups) had significantly increased times of the ICR mouse entered in open arms after the mice were in anxiety state. Similarly, the mice of the experimental groups (i.e. PC, SBO, AC and SZS groups) had significantly reduced times of the ICR mouse entered in closed arms after the mice were in anxiety state as compared with the mice of the control group. Therefore, with respect to the anxiety induced by the closed environment, the mice fed with the Chinese herbal aqueous extracts can significantly increased the times of the mice entered in open arms and reduced the times of the mice entered in closed arms. The results showed that the PC, SBO, AC and SZS aqueous extracts of the Chinese herbal aqueous extracts had physiologically active component of anti-anxiety.

3. Detection of Anti-Anxiety-Related Activities of Central Nervous System of Experimental Animals 3.1 Excision of Brain Tissue All mice were sacrificed after the whole process. The mice brains were excised and cleaned with MEM medium (including 3% FBS, Gibco® BRL, Grand Island, N.Y.). And then, the left and right hippocampuses and the cerebral cortex of each mouse were separated, respectively.

3.2 Primary Cell Culture

The tissue specimens of the mice hippocampuses and cerebral cortexes were homogenized in a tissue culture plate (for example, the plate with diameter of 9 cm). The homogenized tissues were filtrated through 100 μm cell filter and collected in 50 mL centrifuge tube, followed by centrifuging at a centrifugal force of 400×g for 10 minutes by using a centrifuge (BECKMAN Cs-6R, USA). After centrifuging, the supernatant was discarded, and the remained cell layer are added with PBS and adjusted to a cell density of $1\times10^7$/mL, and every 100 μL aliquot ($1\times10^6$/100 μL) of which was added into a 1.5 mL eppendorf vial.

3.3 Detection of CB1 Membrane Expression by Using Fluorescence Antibodies

The eppendorf vials including 100 μL neural cell solution ($1\times10^6$/100 μL) were put on ice. Next, a primary antibodies were added, which included 1 μL rabbit anti-mouse neuron specific enolase (rabbit anti-mouse NSE) antibody (Abcam, Cambridge, UK) for labeling neural cells and 1 μL goat anti-mouse cannabinoid receptor I (CB1) antibody (Abcam, Cambridge, UK) for labeling CBI receptor, so as to detecting the CB1 membrane expression. After mixing the primary antibodies well, the reaction mixture was reacted in the dark for 30 minutes. Afterward, the unbound primary antibodies were washed by thrice repetition of resuspending cells with PBS, centrifuging at a centrifugal force of 400×g for 10 minutes and discarding the supernatant, for completely removing the unbound primary antibodies.

The cell pellets were resuspended with 100 μL PBS and added with secondary antibodies that included 2 μL goat anti rabbit IgG R-phycoerythrin conjugated antibody (Abcam, Cambridge, UK) and 2 μL donkey anti-goat IgG FITC conjugated antibody (Abcam, Cambridge, UK). After mixing the secondary antibodies well, the reaction mixture was reacted in the dark for 30 minutes. Afterward, the unbound secondary antibodies were washed out by thrice repetition of resuspending cells with PBS, centrifuging at a centrifugal force of 400×g for 10 minutes and discarding the supernatant, for completely removing the unbound secondary antibodies. The cell pellets were resuspended and fixed with 500 μL 4% formalin. The CB1 membrane expression of the neural cells was measured by using a FACScan flow cytometry (Beckman Coulter Epics XL-MCL, USA). The flow cytometric results were shown in FIGS. 9A and 9B.

Figure 9A:
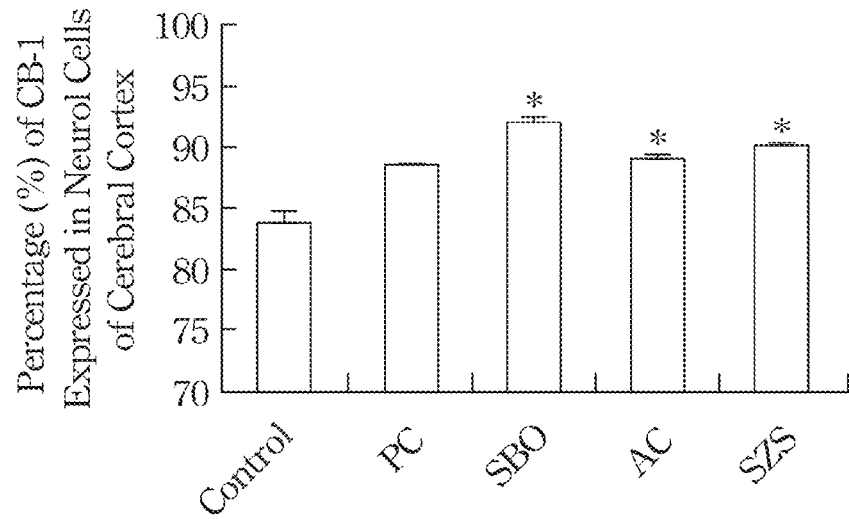
FIGS. 9A and 9B depict histograms of the CB1 membrane expression percentage of neural cells of mice cerebral cortexes (FIG. 9A) and mice hippocampuses (FIG. 9B) according to an embodiment of the present invention.
Figure 9B:
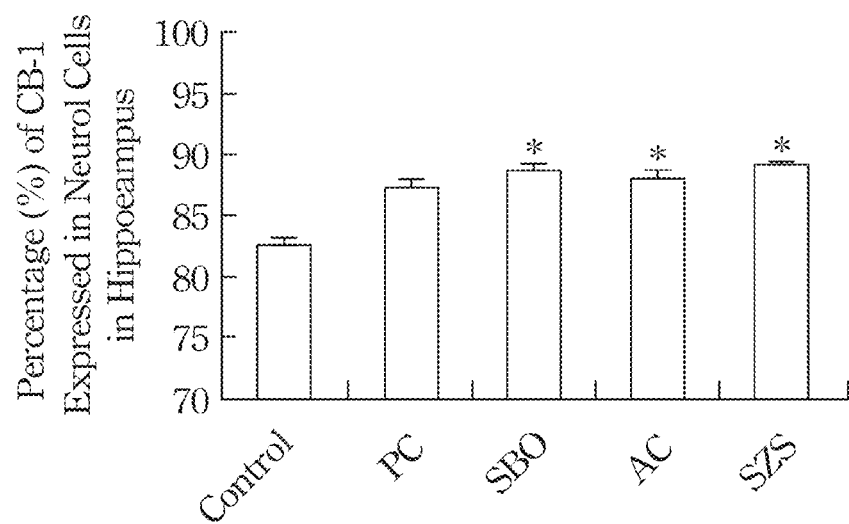

Reference is made to FIGS. 9A and 9B, which depict histograms of the CB1 membrane expression percentage of neural cells of mice cerebral cortexes (FIG. 9A) and mice hippocampuses (FIG. 9B) according to an embodiment of the present invention, in which the control group is referred to the mice fed without Chinese herbal aqueous extracts of EXAMPLE 1, and the symbol "*" is referred to the statically significant difference of the averaged percentage of the experimental group as compared with the control group (i.e. "Control") ($P<0.05$).

Based on the results of FIGS. 9A and 9B, as compared with the mice of the control group that were fed without the Chinese herbal aqueous extracts, the mice of the experimental groups (i.e. PC, SBO, AC and SZS groups) had significantly increased CB1 membrane expression percentage of neural cells of mice cerebral cortexes (FIG. 9A) and mice hippocampuses (FIG. 9B). The results showed that the PC, SBO, AC and SZS aqueous extracts of the Chinese herbal aqueous extracts had physiologically active component of anti-anxiety.

3.4 Detection of Neural Cell Mortality by Using Fluorescence Antibodies

The eppendorf vials including 100 μL neural cell solution ($1\times10^6$/100 μL) were put on ice. Next, 2 μL PI dye was added, mixed well and reacted in the dark for 10 minutes. Afterward, the cells were washed by thrice repetition of resuspending cells with PBS, centrifuging at a centrifugal force of 400×g for 10 minutes and discarding the supernatant. The cell pellets were resuspended with 100 μL PBS and added with a primary antibody, which included 1 μL rabbit anti-mouse neuron specific enolase (rabbit anti-mouse NSE) antibody (Abcam, Cambridge, UK) for labeling neural cells. After mixing the primary antibody well, the reaction mixture was reacted in the dark for 30 minutes. Afterward, the unbound primary antibody was washed by thrice repetition of resuspending cells with PBS, centrifuging at a centrifugal force of 400×g for 10 minutes and discarding the supernatant, for completely removing the unbound primary antibody.

The cell pellets were resuspended with 100 μL PBS and added with a secondary antibody that included 2 μL goat anti rabbit IgG R-phycoerythrin conjugated antibody (Abcam, Cambridge, UK). After mixing the secondary antibody well, the reaction mixture was reacted in the dark for 30 minutes. Afterward, the unbound secondary antibody was washed out by thrice repetition of resuspending cells with PBS, centrifuging at a centrifugal force of 400×g for 10 minutes and discarding the supernatant, for completely removing the unbound secondary antibody. The cell pellets were resuspended and fixed with 500 μL 4% formalin. The fluorescence intensity of the neural cells was measured by using a FACScan flow cytometry (Beckman Coulter Epics XL-MCL, USA), so as to obtain the cell mortality percentages of the neural cells by measuring the proportion of PI stained cells in NSE labeled cells. The NSE labeled cells are referred to neural cells, and the NSE labeled and PI stained cells are referred to necrotic neural cells. The results were shown in FIGS. 10A and 10B.

Figure 10A:
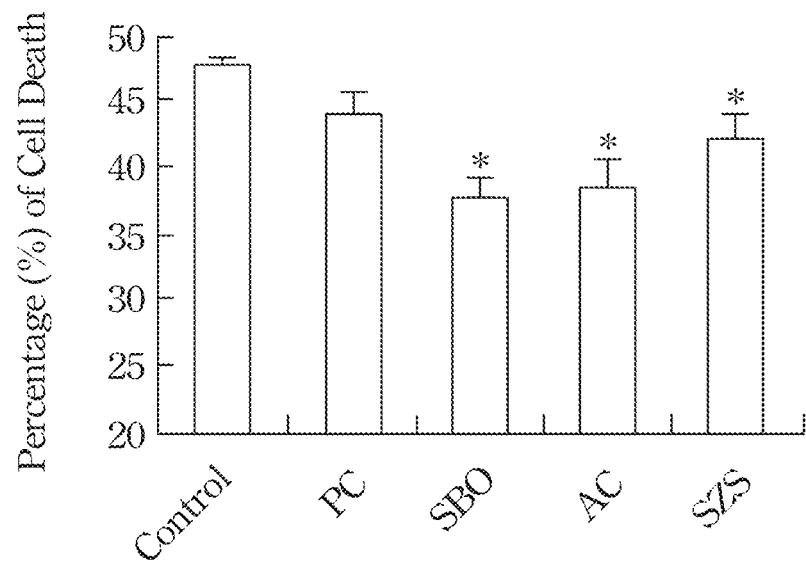
FIGS. 10A and 10B depict histograms of the cell mortality percentage of neural cells of mice cerebral cortexes (FIG. 10A) and mice hippocampuses (FIG. 10B) according to an embodiment of the present invention.
Figure 10B:
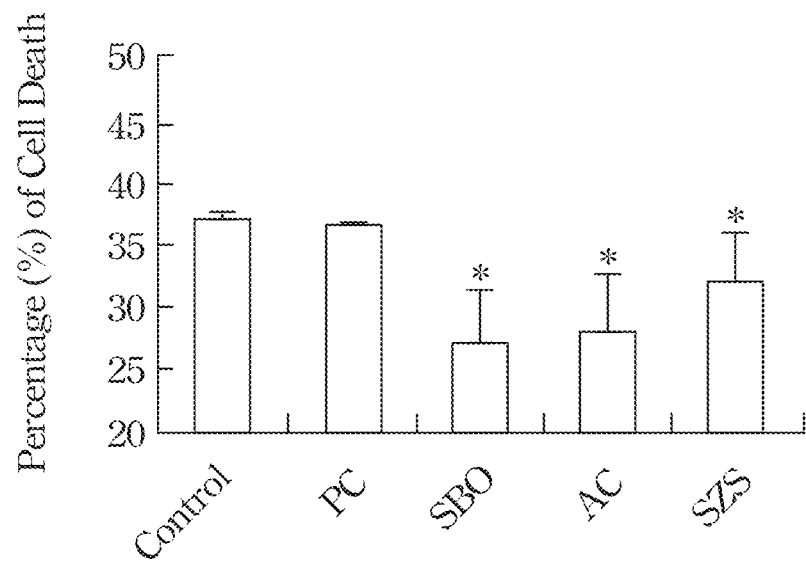

Reference is made to FIGS. 10A and 10B, which depict histograms of the cell mortality percentage of neural cells of mice cerebral cortexes (FIG. 10A) and mice hippocampuses (FIG. 10B) according to an embodiment of the present invention, in which the control group is referred to the mice fed without Chinese herbal aqueous extracts of EXAMPLE 1, and the symbol "*" is referred to the statically significant difference of the averaged percentage of the experimental group as compared with the control group (i.e. "Control") ($P<0.05$).

Based on the results of FIGS. 10A and 10B, as compared with the mice of the control group that were fed without the Chinese herbal aqueous extracts, the mice of the experimental groups (i.e. PC, SBO, AC and SZS groups) had significantly increased cell viability percentage of neural cells of mice cerebral cortexes (FIG. 10A) and mice hippocampuses (FIG. 10B). The results showed that the PC, SBO, AC and SZS aqueous extracts of the Chinese herbal aqueous extracts had physiologically active component of anti-anxiety.

Although the present invention has been described in considerable detail with reference to certain embodiments thereof, other embodiments are possible. It is necessarily supplemented that, specific Chinese herbal aqueous extracts, specific cells, specific extraction process, specific electric pulse treatment, specific experimental animals, specific analysis methods or specific apparatuses are employed as exemplary embodiments for clarifying the Chinese herbal aqueous extract having anti-anxiety activities and method of in vitro evaluating the same of the present invention. However, as is understood by a person skilled in the art, other Chinese herbal aqueous extracts, other cells, other extraction process, other electric pulse treatment, other experimental animals, other analysis methods or other apparatuses can be also employed in the Chinese herbal aqueous extract having anti-anxiety activities and method of in vitro evaluating the same of the present invention, rather than being limited thereto.

In addition, ICR mice further evaluated the biosafety test of aforementioned Chinese herbal aqueous extracts. Sixty-five four-week-old ICR mice were randomly allocated into thirteen groups that included one control (water) group and twelve experimental groups. The experimental groups included four Chinese herbal aqueous extracts, each of which had three different dosages. The dosages of Chinese herbal aqueous extracts in the biosafety test included 0.1 time of recommended intake (0.1×), one time of recommended intake (1×) and ten times of recommended intake (10×), in which one time of recommended intake was defined to 100 mg intake per kg body weight (100 mg/kg body weight). The biosafety test was carried out for 28 days. After the biosafety test was completed, the bloods of all groups were obtained, and biochemical parameters in the bloods were analyzed. The biochemical parameters in the bloods included blood glutamic-pyruvic transaminase (GPT), blood glutamic-oxaloacetic transaminase (GOT), blood urea nitrogen (BUN) and serum creatinine level, for example. The biochemical parameters in the bloods were measured by conventional methods rather than being described in detail. There was no statically significant difference among all groups ($P>0.05$).

Reference is made to TABLE 1, which lists the result of the biosafety test of Chinese herbal aqueous extracts according to an embodiment of the present invention.

TABLE 1

| | GOT (U/L) | GPT (U/L) | BUN (mg/dL) | Creatinine (mg/dL) |
|---|---|---|---|---|
| Control | 106 ± 17 | 62 ± 15 | 21.23 ± 3.67 | 0.83 ± 0.17 |
| 10X PC | 110 ± 16 | 67 ± 14 | 22.16 ± 2.60 | 0.86 ± 0.16 |
| 1X PC | 104 ± 23 | 63 ± 16 | 21.85 ± 2.30 | 0.85 ± 0.16 |
| 0.1X PC | 99 ± 22 | 50 ± 25 | 21.75 ± 2.71 | 0.82 ± 0.06 |
| 10X SBO | 123 ± 13 | 77 ± 13 | 22.58 ± 2.41 | 0.86 ± 0.08 |
| 1X SBO | 114 ± 22 | 69 ± 18 | 21.64 ± 1.78 | 0.85 ± 0.16 |
| 0.1X SBO | 111 ± 5 | 54 ± 11 | 20.92 ± 1.97 | 0.84 ± 0.06 |
| 10X AC | 130 ± 19 | 77 ± 12 | 21.44 ± 4.50 | 0.85 ± 0.04 |
| 1X AC | 128 ± 13 | 54 ± 15 | 20.71 ± 2.75 | 0.86 ± 0.14 |
| 0.1X AC | 102 ± 18 | 50 ± 24 | 21.54 ± 1.06 | 0.84 ± 0.18 |
| 10X SZS | 122 ± 4 | 79 ± 14 | 22.58 ± 1.92 | 0.83 ± 0.07 |
| 1X SZS | 123 ± 19 | 73 ± 7 | 21.44 ± 1.94 | 0.82 ± 0.15 |
| 0.1X SZS | 105 ± 9 | 53 ± 8 | 21.64 ± 2.15 | 0.82 ± 0.13 |

Based on the result of TABLE 1, the evaluated Chinese herbal aqueous extracts had nontoxic to livers and kidneys of the mice. Therefore, a food composition can include the evaluated Chinese herbal aqueous extract alone or mixed with at least one food additive. The kinds and dosage of the food additives are well known by the artisan in the art rather than being described in detail.

According to the embodiments of the present invention, the aforementioned Chinese herbal aqueous extract having anti-anxiety activities and method of in vitro evaluating the same advantageously use the epileptic cells as an evaluation platform for screening the Chinese herbal aqueous extract having anti-anxiety activities. Moreover, the evaluated Chinese herbal aqueous extract indeed has anti-anxiety activities and enhancement of CB1 membrane expression evidenced by the animal experimentation, thereby being applied in food or other compositions.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of in vitro evaluating Chinese herbal aqueous extract with anti-anxiety activity, comprising:
   heating a raw material of a Chinese herbal medicine sample with water and to keep them boiling for 105 minutes, so as to obtain a Chinese herbal aqueous extract, wherein the Chinese herbal aqueous extract is a test sample;
   culturing a neural cell and/or a glial cell in a testing medium that includes the test sample or not for 12 hours to 36 hours, wherein the neural cell and/or the glial cell includes a neural cell line and/or a glial cell line;
   applying an electric pulse treatment on the neural cell and/or the glial cell, allowing the neural cell and/or the glial cell to be suffered with a hyper-excitatory electrical potential injury, thereby forming an epileptic cell;
   detecting at least one anti-anxiety parameter of the epileptic cell, the anti-anxiety parameter comprises a cell viability, a percentage of reactive oxygen species (ROS)-generated cells and a percentage of apoptotic cells, wherein at least one test value is defined to the at least one anti-anxiety parameter obtained from the epileptic cell cultured with the test sample, and at least one reference value is defined to the at least one anti-anxiety parameter obtained from the epileptic cell cultivated without the test sample; and comparing the test value with the reference value, so as to determine that the test sample has the anti-anxiety activity based on when the cell viability is more than the reference value, as well as the percentage of the ROS-generated cells and the percentage of apoptotic cells are less than the reference value.

2. The method of claim 1, wherein the neural cell is human neuroblastoma cell line IMR-32 (deposited at the American Type Culture Collection under accession No.: ATCC CCL-127), and the glial cell is human glioblastoma cell line U-87 MG (deposited at the American Type Culture Collection under accession No.: ATCC HTB-14).

3. The method of claim 1, wherein the neural cell and/or the glial cell is cultured in the testing medium for 24 hours.

4. The method of claim 1, wherein the electric pulse treatment is applied on the neural cell and/or the glial cell by using 5 mV of pulse voltage and 100 ms of inter-pulse interval for 50 times continuously.

5. The method of claim 1, wherein the testing medium includes 0.01 g/L to 1 g/L of the test sample.

6. The method of claim 1, wherein the testing medium includes 0.05 g/L to 0.5 g/L of the test sample.

7. The method of claim 1, wherein the testing medium includes 0.1 g/L of the test sample.

8. The method of claim 1, before obtaining the Chinese herbal aqueous extract, further comprising the step of removing solid components and water from the raw material of the Chinese herbal medicine sample.

9. The method of claim 8, wherein the solid components and water are removed from the raw material of the Chinese herbal medicine sample through a solid-liquid separation process, a reduced pressure concentration process or a lyophilization process.

10. The method of claim 1, wherein the Chinese herbal aqueous extract with anti-anxiety activity is extracted from *Poris Cum* (PC), *Semen Biotae Orientalis* (SBO), *Acanthopanacis Cortex* (AC) or *Semen Zizyphi Spinosae* (SZS).

11. The method of claim 1, wherein a membrane expression of a Cannabinoid receptor type-1 (CB1) is enhanced in vivo by the Chinese herbal aqueous extract with anti-anxiety activity.

* * * * *